United States Patent [19]

Hung

[11] Patent Number: 5,288,910
[45] Date of Patent: Feb. 22, 1994

[54] PALLADIUM CATALYZED ADDITION OF AMINES TO 3,4-EPOXY-1-BUTENE

[75] Inventor: Yann Hung, Rochester, N.Y.

[73] Assignee: Eastman Kodak Company, Rochester, N.Y.

[21] Appl. No.: 940,983

[22] Filed: Sep. 4, 1992

[51] Int. Cl.$^5$ ............................................. C07C 213/00
[52] U.S. Cl. .................................... 564/477; 564/1; 564/399; 564/443; 564/445; 564/462; 564/503
[58] Field of Search ................... 564/475, 477, 1, 399, 564/443, 445, 462, 503

[56] References Cited

U.S. PATENT DOCUMENTS 4,670,557  6/1987  Su ........................................ 564/475

OTHER PUBLICATIONS

B. M. Trost et al., "A Synthesis of Substituted Pyrrolidines via a Palladium(2+)-Catalyzed Cyclization. An Unusual Approach to a Carbapenem," 108 J. Amer. Chem. Soc 6053-4 (1986).

B. M. Trost et al., "Steric Steering with Supported Palladium Catalysts," 100 J. Amer. Chem. Soc. 7779-7781 (1978).

J. Tsuji et al., "Regioselective 1,4-Addition of Nucleophiles to 1,3-Diene Monoepoxides Catalyzed by Palladium Complex," 22 Tetrahedron Letters 2575-8 (1981).

B. M. Trost et al., "Regiochemical Directing Efforts in Palladium Catalyzed Alkylations with Polyene Electrophilic Partners," 27 Tetrahedron Letters 4949-52 (1986).

J. Tsuji et al., "Palladium-Catalyzed Regioselective Reactions of Silyl-Substituted Allylic Carbonates and Vinyl Epoxide," 29 Tetrahedron Letters 343-6 (1988).

J. Tsuji, "New Synthetic reactions Catalyzed By Palladium Complexes," 58 Pure & Applied Chem. 869-78 (1986).

T. Tsuda, "Palladium-Catalyzed Reaction of 1,3-diene Monoepoxides with β-keto Acids. Allylic Alkylation and Isomerization of 1,3-Diene Monoepoxides," 51 J. Org. Chem. 5216-21 (1986).

Trost et al., J. Am. Chem. Soc., vol. 103, pp. 5969-5972 (1981).

Tenaglia et al., Tetrahedron Letters, vol. 29, No. 38, pp. 4851-4854 (1988).

Primary Examiner—Richard L. Raymond
Assistant Examiner—Scott C. Rand
Attorney, Agent, or Firm—J. Frederick Thomsen; William P. Heath, Jr.

[57] ABSTRACT

4-amino-2-buten-1-ol is formed by the regioselective addition of primary amines or ammonia to 3,4-epoxy-1-butene. A quantity of a the primary amine or ammonia is reacted with 3,4-epoxy-1-butene in a reaction medium in the presence of a catalyst. The reaction medium is a liquid which has an $E_T(30)$ no less than about 32. The catalyst is a complex of palladium and phosphine ligands.

21 Claims, No Drawings

PALLADIUM CATALYZED ADDITION OF AMINES TO 3,4-EPOXY-1-BUTENE

FIELD OF INVENTION

A process is disclosed for reacting 3,4-epoxy-1-butene with an amine to produce a 4-amino-substituted-2-buten-1-ol.

BACKGROUND OF THE INVENTION

A variety of 4-aminobutenols are known to have use themselves or as intermediates for the preparation of other chemical substances. For example, 4-dimethylamino-2-buten-1-ol could be used in the preparation of 4-dimethylaminobutyraldehyde diethyl acetal, an intermediate for a pharmaceutical compound, as disclosed in German Patent No. 3,700,408.

3,4-Epoxy-1-butene (butadiene monoepoxide) is one potential substrate for the production of 4-aminobutenols. However, the reaction of nitrogen nucleophiles (e.g., amines) with 3,4-epoxy-1-butene typically yields a mixture of the 1,2 addition product (1,2 adduct) and the 2,1 addition product (2,1 adduct), and little or none of the 1,4 addition product (1,4 adduct). The reaction is illustrated below:

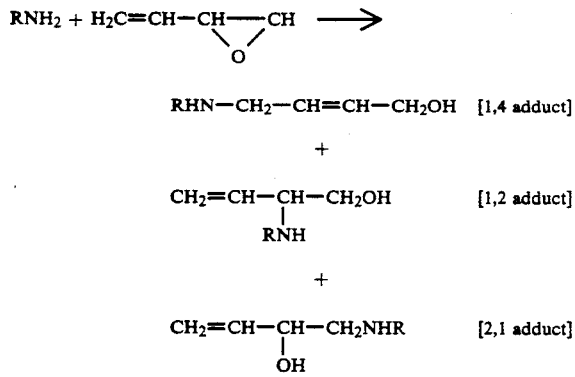

See, e.g., M.G. Ettlinger, "Synthesis of the Natural Antithyroid Factor 1-5-Vinyl-2-Thiooxazolidone", 72 J. Amer. Chem. Soc. 4792-4795 (1950); U.S. Pat. No. 2,533,085 to Blicke; W.B. Wheatley, et al., "o-Benzylphenyl Derivatives. IV. beta-Chloro-ethylamines", 72 J. Amer. Chem. Soc. 1655-1659 (1950); M.P. Crozet and W. Kassar, "Synthesis and Radical Cyclization of Benzazepinoethane Thiols", 99 Compte Rendu Acad. Sci. Paris 99-101 (1985); U.S. Pat. No. 2,497,553 to Long, Jr.; A.A. Petrov and V.M. Albitskaya, "The Reaction of Divinyloxide with Amines", 26 Zhur. Obshchei Khim. 2125-2127 (1956); and F.F. Blicke and J.H. Biel, "Aminolysis Products of 1-Chloro-2-Hydroxy-3-butene, 1-Hydroxy-2-Chloro-3-butene and 1,2-Epoxy-3-butene", 79 J. Amer Chem. Soc. 5508-12 (1957).

The regioselective addition of nitrogen nucleophiles to substrates to form 4-aminobutenols (the 1,4 adduct product) is extremely unpredictable in both result and yield. For example, in Tsuji, et al., "Regioselective 1,4-Addition of Nucleophiles to 1,3-Diene Monoepoxides Catalyzed by Palladium Complex", 22 Tetrahedron Letters 2575-78 (1981) the formation of the 1,4 adduct from the palladium catalyzed reaction of 3,4-epoxy-1-dodecene and pyrrolidine is disclosed. Also, Trost, et al., "A Synthesis of Substituted Pyrrolidines via a Palladium(2+) Catalyzed Cyclization. An Unusual Approach to a Carbapenem", 108 J. Amer. Chem. Soc. 6053-54 (1986) discloses the formation of the 1,4 adduct from the addition of a nitrogen nucleophile to 3,4-epoxy-1-butene. On the other hand, Tsuda, et al., "Palladium(0)-Catalyzed Reaction of Methyl-γ,δ-epoxysorbate with Nitrogen Nucleophiles", 54 Journal of Organic Chemistry 977-979 (1989) discloses that the palladium-catalyzed reaction of methyl-γ,δ-epoxysorbate with nitrogen nucleophiles is not regioselective for the 1,4 adduct.

It is widely recognized that the control of regiochemistry in the addition of nucleophiles to an intermediate unsymmetrical allyl-palladium substrate is an extremely complex problem. Many factors enter into the determination of which terminus of the electrophilic allyl ligand the nucleophile will preferentially attack. These factors include the steric nature of the nucleophile (see B.M. Trost, et al., "Allylic Alkylation: Nucleophilic Attack on pi-Allyl palladium Complexes", 100 J. Amer. Chem. Soc. 3416 (1978)) and the allyl substrate (see E. Keinen, et al. "Regioselectivity in Organo-transitionmetal Chemistry. A Remarkable Steric Effect in pi-Allyl Palladium Chemistry", J. Chem. Soc., Chem. Commun., 648 (1984)); the electronic nature of the allyl substrate on the palladium (see J. Tsuji, et al., "Palladium-Catalyzed Regioselective Reactions of α-Acetoxy-β, γ-Unsaturated Nitriles and γ-Acetoxy-α, β-Unsaturated Ester with Nucleophiles," 22 Tetrahedron Letters 2573 (1981)); the electronic nature of the other ligands on the palladium (see B. Akermark, et al., "Reactivity and syn-anti Isomerization of η-3-geranyl and η-3-neryl Palladium Complexes. Evidence for Electronic Control of the Regiochemistry of Nucleophilic Addition", 4 Organometallics 1275 (1985)); and the mechanism of the addition of the nucleophile (see Godleski, et al., "(pi-Allyl)Palladium Complexes of Norcamphene. Structure and Reactivity", 3 Organometallics 21 (1984)).

Therefore, in light of the usefulness of 4-amino-substituted-2-buten-1-ols derived from 3,4-epoxy-1-butene and the inherent unpredictability of the result (relative to both the product and the yield) of attempted regioselective amine additions to 3,4-epoxy-1-butene, there continues to be a need for predictable, efficient synthetic processes for deriving 4-amino-substituted-2-buten-1-ols from 3,4-epoxy-1-butene. Even small relative increases in the yield of the 1,4 adduct from amine addition to 3,4-epoxy-1-butene can translate into large cost savings when the increase is extrapolated out to production scale.

SUMMARY OF THE INVENTION

A process for producing improved yields of 4-amino-substituted-2-buten-1-ols is disclosed. More particularly, the palladium-catalyzed 1,4 addition of amines to 3,4-epoxy-1-butene is described. The present process includes the steps of reacting a quantity, of 3,4-epoxy-1-butene with a quantity of a primary amine or ammonia in a reaction medium and in the presence of a catalyst. The catalyst utilized in the present process is a complex of palladium and phosphine ligands. The reaction medium used in the process of the present invention is a liquid having an $E_T(30)$ no less than about 32. Preferably, the reaction medium has an $E_T(30)$ no less than about 40, and, most preferably, no less than about 45.

The present invention provides a method for forming 4-amino-substituted-2-buten-1-ols with a greater degree of regioselectivity and in yields that, especially at production levels, are significantly improved.

DETAILED DESCRIPTION OF THE INVENTION

The process of the present invention relates to the formation of 4-amino-substituted-2-buten-1-ols from 3,4-epoxy-1-butene. The process includes the steps of providing a quantity of 3,4-epoxy-1-butene and a quantity of a primary amine or ammonia. The amine or ammonia and the 3,4-epoxy-1-butene are reacted in a reaction medium in the presence of a catalyst. The catalyst is a complex of palladium ("Pd") and phosphine ligands. The reaction medium used in the process of the present invention is a liquid having an $E_T(30)$ no less than about 32. Preferably, the reaction medium has an $E_T(30)$ no less than about 40, and, most preferably, no less than about 45.

The 3,4-epoxy-1-butene used in the present method can be synthesized by any conventional process. Preferred processes for the preparation of 3,4-epoxy-1-butene are disclosed in U.S. Pat. Nos. 4,897,498 and 4,950,773, both to Monnier et al.

Primary amines useful in the present method have the general formula R-NH$_2$, wherein R is a substituted or unsubstituted alkyl group having from one to 10 carbons, a functionalized alkyl group having from one to 10 carbons, a substituted or unsubstituted aryl group, or a substituted or unsubstituted cycloalkyl group. Examples of useful primary amines include methylamine, ethylamine, propylamine, butylamine, hexylamine, octylamine, decylamine, allylamine, 2-hexenylamine, 4-decenylamine, ethanolamine, octanolamine, aniline, and cyclohexylamine.

The reaction medium used in the present method is a liquid having an $E_T(30)$ no less than about 32 as measured by a method disclosed in C. Reichardt, *Solvent Effects in Organic Chemistry*, pp. 242–244 (1979) ("Reichardt"), the disclosure of which is hereby incorporated by reference. $E_T(30)$ is defined according to Reichardt as the transition energy for the solvatochromic absorption band with the longest wavelength of the dye 2,6-diphenyl-4-(2,4,6-triphenyl-1-pyridino) phenoxide, as measured at 25° C. and 760 torr. The $E_T(30)$ value quantifies the polarity of a reaction medium and takes into account both the dielectric constant, dipole moment, and the degree of hydrogen bonding exhibited by the liquid. Generally, the higher the $E_T(30)$, the more polar the liquid. It has been discovered in accordance with the present invention that reaction media exhibiting a high degree of hydrogen bonding in combination with a high dielectric constant and/or dipole moment allow for the greatest regioselectivity for the 1,4-adduct of the addition reaction of primary amines to 3,4-epoxy-1-butene.

Reaction media useful in the present method (and their $E_T(30)$) include, but are not limited to, toluene (33.9), benzene (34.5), diethylether (34.6), 1,4-dioxane (36.0), tetrahydrofuran (37.4), chloroform (39.1), acetone (42.2), dimethylsulfoxide (45.0), acetonitrile (46.0), nitromethane (46.3), 2-propanol (48.6), ethanol (51.9), 2-methoxyethanol (52.3), N-methylformamide (54.1), methanol (55.5), 1,2-ethanediol (56.3), glycerol (57.0), 2,2,2-trifluoroethanol (59.5), and water (63.1). Preferably, the reaction medium has an $E_T(30)$ not less than about 40, most preferably not less than about 45. The best reaction medium is water because of its high dielectric constant and very high degree of hydrogen bonding. Other useful reaction media include liquid methylamine and combinations of liquids such as water combined with an organic solvent. Preferably, the combination includes water. An especially useful mixed reaction medium is an 80:20 solution of ethanol and water, which has an $E_T(30)$ of 53.7.

The catalyst utilized in the present method is a complex of palladium and phosphine ligands. The catalyst selection should be based on the nature of the reaction medium used. Preferably, the catalyst should be substantially soluble in the reaction medium to maximize the catalyst's activity. For example, if water is the reaction medium, a water soluble palladium catalyst is preferred. On the other hand, if the reaction medium is less polar than water (e.g., an organic solvent) the catalyst is preferably substantially soluble in that medium. If the palladium catalyst has phosphine ligands that are in their liquid state at the reaction temperature, the relative solubility of the catalyst is not critical.

The catalyst can either be added to the reaction medium in a catalytically active form or in the form of precursors that are added separately to the reaction medium and become catalytically active in situ. If added as precursors, the catalyst precursors include a palladium precursor and phosphine ligands. The palladium precursor and the phosphine ligands are mixed in a small amount of a solvent (which both are soluble in) to form the catalyst in situ. This catalyst solution is then added to the reaction medium. When the catalyst is in the form of catalyst precursors, the phosphine ligands utilized in conjunction with the palladium precursor have the general formula PR$_1$R$_2$R$_3$, wherein P is phosphorus and R$_1$, R$_2$, and R$_3$ can be the same or different and each are an alkyl, cycloalkyl, alkoxide, aryl, heterocyclic, functionalized alkyl, functionalized aryl, or ether group.

For the purposes of the present invention, useful palladium catalysts have been grouped into eight general categories (i.e., Categories I–VIII). Within the description of each category, Q is a cation such as Na$^+$, K$^+$, Li$^+$, (CH$_3$)$_4$N$^+$, NH$_{4+}$, and the like. X is an anion such as Cl$^-$, Br$^-$, NO$_3^-$, NO$_2^-$, N$_3^-$, BF$_4^-$, OH$^-$, SCN$^-$, $\beta$-diketonate, carboxylate, and the like. Ph represents a phenyl group. P is phosphorus and Pd is palladium. a is a number in the range from 1 to 3; b is a number in the range from 1 to 4; c and f are 1 or 2; d is a number in the range from 2 to 4; and e is either 12 or 16. R$_1$, R$_2$, and R$_3$ are defined above.

Category I palladium catalysts have the formula Pd(PR$_1$R$_2$R$_3$)$_2$X$_2$. Useful Category I catalysts include, for example, Pd(PPh$_3$)$_2$X$_2$, Pd(P(p-tolyl)$_3$)$_2$X$_2$, Pd(PhP(C$_2$H$_4$CN)$_2$)$_2$X$_2$, and Pd(P(C$_2$H$_4$CN)$_3$)$_2$X$_2$. Especially useful Category I catalysts include Pd(Ph$_2$P(m-C$_6$H$_4$SO$_3$Q))$_2$X$_2$, Pd(P(m-C$_6$H$_4$SO$_3$Q)$_3$)$_2$X$_2$, Pd(Ph$_2$P(o-CO$_2$C$_6$H$_4$Q))$_2$X$_2$, Pd(P(CH$_2$(CH$_2$CH$_2$O)$_a$CH$_3$)$_3$)$_2$X$_2$, Pd(PhP(CH$_2$CH$_2$CH$_2$OCH$_3$)$_2$)$_2$X, Pd(Ph$_2$PCH$_2$CH$_2$N(CH$_3$)$_3$X)$_2$X$_2$, Pd(Ph$_2$PCH$_2$CH$_2$CO$_2$Q)X$_2$, and the like. The preparation of Category I catalysts is described in D. Hedden et al, "Synthesis of New Hybrid Phosphine Amine and Phosphine Amide Compounds. Preparation of a Series of New Phosphine Amido Chelate Compolexes of Palladium (II) and Platinum (II) and Their Reactions with Bases and Bronsted Acids", 24 *Inorg. Chem.*, 4152–4158 (1985) and C. Larpent and H. Patin, "Hydrosoluble Transition-metal Coordination Compounds of Triphenylphosphine m-Trisulfonate". 1 *Appl. Organomet. Chem.* 529 (1987).

Category II catalysts have the general formula $Pd(R_4R_5P(V)_bZR_6R_7)X_2$ wherein V is $CH_2$ or CH as part of unsaturated component; Z is phosphorus or nitrogen; and $R_4$, $R_5$, $R_6$, and $R_7$ can be the same or different and each are an alkyl, cycloalkyl, alkoxide, aryl, heterocyclic, functionalized alkyl, functionalized aryl, or ether group. Useful Category II catalysts include $Pd[(C_6H_5)_2P(CH_2)P(C_6H_5)_2]X_2$, $Pd[(C_6H_5)_2P(CH_2)_2P(C_6H_5)_2]X_2$, $Pd[(C_6H_5)_2P(CH_2)_3P(C_6H_5)_2]X_2$, $Pd[(C_6H_5)_2P(CH_2)_4P(C_6H_5)_2]X_2$, $Pd[(p-tolyl)_2P(CH_2)P(p-tolyl)_2]X_2$, $Pd[(p-tolyl)_2P(CH_2)_2P(p-tolyl)_2]X_2$, $Pd[(C_6F_5)_2P(CH_2)_2P(C_6F_5)_2]X_2$, $Pd[(NCC_2H_4)_2PC_2H_4P(C_2H_4CN)_2]X_2$, and the like. Especially useful Category II catalysts include $Pd[(C_6H_5)_2P(CH_2)_2N(CH_3)_2]X_2$, $Pd[(m-SO_3C_6H_4Q)_c(C_6H_5)_{2-c}P(CH_2)_dP(C_6H_5)_f(m-SO_3C_6H_4Q)_{2-f}]X_2$, $Pd[(m-SO_3C_6H_4Q)_c(C_6H_5)_{2-c}PCH(CH_3)CH(CH_3)P(C_6H_5)_f(m-SO_3C_6H_4Q)_{2-f}]X_2$, $Pd[(p-(CH_3)_3NC_6H_4X)_2PC_2H_4P(p-(CH_3)_3NC_6H_4X)_2]X_2$, $Pd[(p-(CH_3)_3NC_6H_4X)_2PCH(CH_3)CH(CH_3)P(p-(CH_3)_3NC_6H_4X)_2]X_2$, and

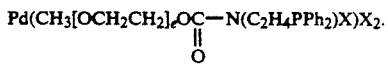

The preparation of Category II catalysts is described in M.J. Hudson, et al, "Ditertiary Arsine and Phosphine Compounds of Nickel (II), Palladium (II), and Platinum (II)", *J. Chem. Soc.*, A, 40 (1968).

Category III catalysts have the general formula $[(\eta^3-CH(R_8)C(R_9)CH(R_{10}))Pd(PR_1R_2R_3)_2]X$, wherein $R_8$, $R_9$, and $R_{10}$ are the same or different and each are hydrogen, alkyl, cycloclkyl, aryl, heterocyclic, halogen, ether, sulfide, carbonyl or are linked together to form a ring. Useful category III catalysts include $[(\eta^3-C_3H_5)Pd(PPh_3)_2](X)$, $[(\eta^3-C_3H_5)Pd(P(p-tolyl)_3)_2](X)$, $[(\eta^3-C_3H_5)Pd(P(C_4H_3O)_3)_2](X)$, and the like. Especially useful Category III palladium catalysts include $[(\eta^3-C_3H_5)Pd(P(m-C_6H_4SO_3Q)_3)_2](X)$, $[(\eta^3-C_3H_5)Pd(Ph_2P(m-C_6H_4SO_3Q))_2](X)$, $[(\eta^3-C_3H_5)Pd(Ph_2P(m-C_6H_4CO_2Q))_2]X$, $[(\eta^3-C_3H_5)Pd(P(CH_2(CH_2CH_2O)_aCH_3)_3)_2]X$, $[(\eta^3-C_3H_5)Pd(PhP(CH_2CH_2CH_2OCH_3)_2)_2]X$, $[(\eta^3-C_3H_5)Pd(Ph_2PCH_2CH_2N(CH_3)_3X)_2]X$, $[(\eta^3-C_3H_5)Pd(P(O-iso-C_3H_7)_3)_2]X$, and the like.

Category IV catalysts have the general formula $[(\eta^3-CH(R_8)C(R_9)CH(R_{10}))Pd(R_4R_5P(V)_bZR_6R_7]X$, wherein $R_4$, $R_5$, $R_6$, $R_7$, V, and Z have the same meanings as described above for the Category II catalysts; and $R_8$, $R_9$, and $R_{10}$ have the same meanings as described above for the Category III catalysts. Useful Category IV catalysts include $[(\eta^3-C_3H_5)Pd(C_6H_5)_2P(CH_2)P(C_6H_5)_2](X)$, $[(\eta^3-C_3H_5)Pd(C_6H_5)_2P(CH_2)_2P(C_6H_5)_2](X)$, $[(\eta^3-C_3H_5)Pd(C_6H_5)_2P(CH_2)_3P(C_6H_5)_2](X)$, and the like. Especially useful Category IV catalysts include $[(\eta^3-C_3H_5)Pd[(m-SO_3C_6H_4Q)_c(C_6H_5)_{2-c}P(CH_2)_dP(C_6H_5)_f(m-SO_3C_6H_4Q)_{2-f}]X$, $[(\eta^3-C_3H_5)Pd(p-(CH_3)_3NC_6H_4X)_2PC_2H_4P(p-(CH_3)_3NC_6H_4X)_2]X$, $[(\eta^3-C_3H_5)Pd(p-(CH_3)_3NC_6H_4X)_2PCH(CH_3)CH(CH_3)P(p-(CH_3)_3NC_6H_4X)_2]X$. The preparation of Category III and IV catalysts is described in B. Akermark, et al, "Ligand Effects and Nucleophilic Addition to ($\eta^3$-allyl)Palladium Complexes. A Carbon-13 Nuclear Magnetic Resonance Study", 6 *Organometallics* 620 (1987).

Category V catalysts have the general formula $Pd(R_4R_5P(V)_bZR_6R_7)_2$, wherein $R_4$, $R_5$, $R_6$, $R_7$, V, and Z are as described above for Category II catalysts. Useful Category V catalysts include $Pd[(C_6H_5)_2P(CH_2)_2P(C_6H_5)_2]_2$, and the like. Especially useful Category V catalysts include $Pd[(C_6H_5)_2P(CH_2)_2N(CH_3)_2]_2$, $Pd[(p-(CH_3)_3NC_6H_4X)_2PCH(CH_3)CH(CH_3)P(p-(CH_3)_3NC_6H_4X)_2]_2$, $Pd[(p-(CH_3)_3NC_6H_4X)_2PC_2H_4P(p-(CH_3)_3NC_6H_4X)_2]_2$, and $Pd[(m-SO_3C_6H_4Q)_c(C_6H_5)_{2-c}P(CH_2)_dP(C_6H_5)_f(m-SO_3C_6H_4Q)_{2-f}]_2$.

Category VI catalysts have the general formula $Pd(PR_1R_2R_3)_4$. Useful Category VI catalysts include $Pd(P(m-C_6H_4SO_3Q)_3)_4$, $Pd[Ph_2P(m-SO_3C_6H_4Q)]_3$, $Pd[Ph_2P(m-SO_3C_6H_4Q)]_4$, $Pd[P(CH_2(CH_2CH_2O)_aCH_3)_3]_4$, $Pd[P(CH(CH_3)(CH_2CH_2O)_3CH_3)_3]_4$, $Pd[PhP(CH_2CH_2CH_2OCH_3)_2]_4$, and $Pd[Ph_2PCH_2CH_2N(CH_3)_3X]_4$. The preparation of Category V and VI catalysts is described in A.L. Casalnuovo and J.C. Calabrese, "Palladium-Catalyzed Aklylation in Aqueous Media", 112 *J. Amer. Chem. Soc.* 4324 (1990).

Category VII catalysts have the general formula $[Pd(D)(PR_1R_2R_3)_2]X_2$, wherein D is a cyclic diene. Useful Category VII catalysts include $[(C_8H_{12})Pd(PPh_3)_2]X_2$, and $[(C_7H_8)Pd(PPh_3)_2]X_2$ (wherein the cyclic diene is bicyclo[2,2,1]hepta-2,5-diene) and cis,cis-1,5-cyclo-octadiene. Especially useful Category VII catalysts include $[(C_8H_{12})Pd(P(m-C_6H_4SO_3Q)_3)_2]X_2$, $[(C_8H_{12})Pd(Ph_2P(m-C_6H_4SO_3Q))_2]X_2$, $[(C_7H_8)Pd(P(CH_2(CH_2CH_2O)_aCH_3)_3)_2]X_2$, $[(C_7H_8)Pd(PhP(CH_2CH_2CH_2OCH_3)_2)_2]X_2$, $[(C_7H_8)Pd(Ph_2PCH_2CH_2N(CH_3)_3X)_2]X_2$, $[(C_7H_8)Pd((C_6H_5)_2P(m-SO_3C_6H_4Q))_2]X_2$, $[(C_7H_8)Pd(P(m-SO_3C_6H_4Q)_3)_2]X_2$, $[(C_8H_{12})Pd(P(CH_2(CH_2CH_2O)_aCH_3)_3)_2]X_2$, and $[(C_8H_{12})Pd(PhP(CH_2CH_2CH_2OCH_3)_2)_2]X_2$ Category VIII catalysts have the general formula $[Pd(D)(R_4R_5P(V)_bZR_6R_7)]X_2$, wherein D is as described above for Category VII, and $R_4$, $R_5$, $R_6$, $R_7$, V, and Z are as described above for Category II. Useful Category VIII catalysts include $(C_7H_8)Pd(C_6H_5)_2P(CH_2)_bP(C_6H_5)_2]X_2$, and $(C_8H_{12})Pd(C_6H_5)_2P(CH_2)_bP(C_6H_5)_2]X_2$. Especially useful Category VIII catalysts include $(C_7H_8)Pd((p-(CH_3)_3NC_6H_4X)_2PCH(CH_3)CH(CH_3)P(p-(CH_3)_3NC_6H_4X)X_2$, $[(C_7H_8)Pd(m-SO_3C_6H_4Q)_c(C_6H_5)_{2-c}P(CH_2)_dP(C_6H_5)f(m-SO_3C_6H_4Q)_{2-f}]X_2$, $[(C_7H_8)Pd(p-(CH_3)_3NC_6H_4X)_2PC_2H_4P(p-(CH_3)_3NC_6H_4X)_2]X_2$, $[(C_7H_8)Pd(CH_3[OCH_2CH_2]_aOC-N(C_2H_4PPh_2)_2)]X_2$, $[(C_7H_8)Pd(m-SO_3C_6H_4Q)_c(C_6H_5)_{2-c}PCH(CH_3)CH(CH_3)P(C_6H_5)f(m-SO C_6H_4Q)_{2-f}]X_2$, $[(C_8H_{12})Pd((p-(CH_3)_3NC_6H_4X)_2PCH(CH_3)CH(CH_3)P(p-(CH_3)_3NC_6H_4X)_2]X_2$, $[(C_8H_{12})Pd(p-(CH_3)_3NC_6H_4X)_2PC_2H_4P(p-(CH_3)_3NC_6H_4X)_2]X_2$,

[(C₈H₁₂)Pd(CH₃[OCH₂CH₂]ₑOC—N(C₂H₄PPh₂)₂)]X₂,

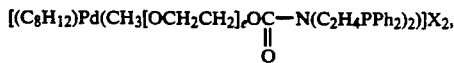

[(C₈H₁₂)Pd(m-SO₃C₆H₄Q)ₑ(C₆H₅)₂₋ₑP(CH₂)ₐP(C₆H₅)ₑ(n-SO₃C₆H₄Q)₂₋ₑ]X₂, [(C₈H₁₂)Pd(m-SO₃C₆H₄Q)ₑ(C₆H₅)₂₋ₑPCH(CH₃)CH(CH₃)P(C₆H₅)ₑ(m-SO₃C₆H₄Q)₂₋ₑ]X₂. The preparation of Category VII and Category VIII catalysts is described in D.A. White, "Cationic Diene Complexes of Palladium (II) and Platinum (II)", v. XIII Inorg. Synthesis. 56 (1972).

The amount of the amine or ammonia incorporated into the reaction medium can vary up to the primary amine's or ammonia's solubility limit. In fact, the proportions of the reactants and the catalyst can all be varied widely while still obtaining the desired product in high yield. Preferably, the concentration of primary amine or ammonia in the reaction medium is at least about 0.1M, most preferably at least about 1.0M.

Generally, because palladium is a precious metal, low concentrations of catalyst are preferred. Catalyst concentrations as low as 0.1 mole percent, based on 3,4-epoxy-1-butene, can be used. Preferably, the catalyst concentration is at least about 0.1 mole percent, most Preferably at least about 0.26 mole percent, based on the quantity 3,4-epoxy-1-butene used. The catalyst concentration is normally less than about 20 mole percent, preferably, less than 10 mole percent, based on the quantity 3,4-epoxy-1-butene used.

The molar ratio of primary amine or ammonia to 3,4-epoxy-1-butene can also vary over wide ranges. Molar ratios from 1:1 to 100:1, preferably 5:1 to 100:1, can be used. To maximize the conversion of 3,4-epoxy-1-butene and also prevent the consecutive addition of 4-amino-2-buten-1-ol itself to 3,4-epoxy-1-butene, an excess of the primary amine or ammonia should be present. Therefore, a particularly preferred range of primary amine or ammonia to 3,4-epoxy-1-butene is in the range from about 10:1 to 100:1.

The conversion of 3,4-epoxy-1-butene can occur in a temperature range from about −6° to 100° C. Preferably, the reaction is performed at room temperature, although mild heating can be used to accelerate the reaction. The amine partial pressure can be increased to greater than five times the atmospheric pressure to eliminate unwanted products and increase the reaction rate. The invention is further illustrated by the following non-limiting examples.

EXAMPLES

EXAMPLE 1

Methylamine addition to 3,4-epoxy-1-butene catalyzed by tetrakistriphenylphosphine palladium(0)

A stock solution of methylamine dissolved in tetrahydrofuran ("THF") was prepared by bubbling methylamine into dry, chilled THF with a dry ice-acetone cold trap. The concentration of methylamine in the stock solution was 6M.

A control reaction was performed by dissolving 0.05g of tetrakistriphenylphosphine palladium(0) catalyst in 0.5 ml dry THF under an argon atmosphere. 2 ml of the 6M methylamine-THF stock solution was added to the dissolved catalyst mixture to form a reaction mixture. The air and oxygen were removed by conventional freeze-thaw techniques. 0.035 ml 3,4-epoxy-1-butene was then added to the degassed reaction mixture. The reaction mixture was kept at 30° C. for 20 hours. The product of the reaction was analyzed by gas chromatogrpahy. The major products of the reaction were a combination of 2,5-divinyl-1,4-dioxane and 2,6-divinyl-1,4-dioxane (60 mole percent). 4-methylamino-2-buten-1-ol (1,4 adduct) and 2-methylamino-3-buten-1-ol (1,2 adduct) were present in a concentration of 23 mole percent of the reaction product. The relative ratio of 1,4 adduct to 1,2 adduct was 0.4.

EXAMPLE 2

Methylamine addition to 3,4-epoxy-1-butene catalyzed by [(η³-C₃H₅)Pd(L)₂](BF₄) in tetrahydrofuran Methylamine was reacted with 3,4-epoxy-1-butene in the presence of a catalyst having the general formula [(η³-C₃H₅)Pd(L)₂](BF₄), wherein L is a phosphine ligand. 0.014 g of [(η³-C₃H₅)Pd(CH₃CN)₂](BF₄) was mixed with a series of phosphine ligands as shown in Table I in 0.2 ml of dry THF under an argon atmosphere to form the catalyst of the sample in situ. Each of the ligands shown were purchased from Strem Chemicals, Inc., Newburyport, Mass with the exception of P(C₄H₃O)₃ which was prepared according to procedures described in D. Allen et al., "The Chemistry of Heteroarylphosphorus Compounds. Part II. The Importance of Inductive Effects on Pre-equilibria in the Alkaline Hydrolysis of Heteroarylphosphonium Salts; Phosphorus-31 Nuclear Magnetic Resonance Studies,"J. Chem. Soc. Perkin II, 63 (1972). 2 ml of a methylamine-THF stock solution prepared according to Example 1 was added to the catalyst mixture to form a reaction mixture. The reaction mixture was degassed by freeze-thaw three times. 0.035 ml 3,4-epoxy-1-butene was then added to the degassed reaction mixture which was kept at 30° C. for 20 hours. The reaction product was analyzed by gas chromatography, Table I below illustrates the ratio of the amount of 1,4 adduct formed relative to the amount of the 1,2 adduct formed ("1,4:1,2").

TABLE I

| Sample | Ligand | Amount of Ligand (eq.) | 1,4:1,2 |
|---|---|---|---|
| 1 | P(C₆H₅)₃ | 2 | 1.7 |
| 2 | P(C₆H₅)₃ | 4 | 2.4 |
| 3 | P(p-tolyl)₃ | 4 | 2.9 |
| 4 | (C₆H₁₁)(C₆H₅)₂P | 4 | 1.1 |
| 5 | P(C₄H₃O)₃ | 4 | 1.3 |
| 6 | (C₆H₅)₂P(CH₂)₂P(C₆H₅)₂ | 2 | 2.9 |
| 7 | (C₆H₅)P(CH₂CH₂CN)₂ | 2 | 2.3 |
| 8 | (C₆H₅)₂P(CH₂)₂N(CH₃)₂ | 2 | 1.6 |
| 9 | P(CH₂CH₂PPh₂)₃ | 1 | 2.5 |
| 10 | o-C₆H₄[P(C₆H₅)₂]₂ | 2 | 2.5 |
| 11 | (C₆F₅)₂P(CH₂)₂P(C₆F₅)₂ | 2 | 2.2 |
| 12 | cis-(C₆H₅)₂PCH=CHP(C₆H₅)₂ | 2 | 2.1 |
| 13 | (C₆H₅)₂P(CH₂)₃P(C₆H₅)₂ | 2 | 2.5 |
| 14 | (C₆H₅)₂PCH₂P(C₆H₅)₂ | 2 | 2.2 |

As compared to Example 1 (THF as reaction medium and tetrakistriphenylphosphine palladium (0) as catalyst), the reaction ran without the formation of undesirable products, i.e., no 2,5- or 2,6-divinyl-1,4-dioxane. In addition, the ratio of 1,4-adduct as compared to 1,2-adduct was dramatically increased over the 0.4:1 ratio seen in Example 1.

EXAMPLE 3

Methylamine addition to 3,4-epoxy-1-butene catalyzed by [($\eta^3$-C$_3$H$_5$)Pd((C$_6$H$_5$)$_2$P(m-SO$_3$C$_6$H$_4$Na))$_2$](BF$_4$) in liquid methylamine 2 ml of methylamine was condensed into a glass reaction tube equipped with Young's stopcock. The glass tube was capable of holding pressures greater than 2 atmospheres. 0.01 g of [($\eta^3$-C$_3$H$_5$)Pd((C$_6$H$_5$)$_2$P(m-SO$_3$C$_6$H$_4$Na))$_2$](BF$_4$) was dissolved in the liquid methylamine. [(C$_6$H$_5$)$_2$P(m-SO$_3$C$_6$H$_4$Na) was synthesized following the procedure by Ahrland et al "The Relative Affinities of Co-ordinatig Atoms for Silver Ion. Part II. Nitrogen, Phosphorus, and Arsenic." *J. Chem. Soc.*, 276 (1958)]0.08 ml 3,4-epoxy-1-butene was added and the reaction solution was stirred at room temperature for four hours and excess methylamine was evaporated. The residue was dissolved in CDCl$_3$ and nmr analysis was performed. The ratio of 1,4-adduct to 1,2-adduct was 6:1. This ratio was a large increase over the 0.4:1 ratio of 1,4-adduct to 1,2-adduct seen in Example 1.

EXAMPLE 4

Methylamine addition to 3,4-epoxy-1-butene using water as the reaction medium.

Methylamine was reacted with 3,4-epoxy-1-butene in the presence of various catalysts using water as the reaction medium. Each representative catalyst was dissolved in 0.5 ml water. 1.8 ml of a 40 weight percent solution of methylamine in water was added to the reaction solution, followed by 0.08 ml 3,4-epoxy-1-butene to give an amine to 3,4-epoxy-1-butene molar ratio of 20:1, except in Sample 15, where 2 ml of the methylamine/water solution and 0.35 ml 3,4-epoxy-1-butene were added to increase the ratio to 50:1. In each sample, the molar ratio of catalyst to 3,4-epoxy-1-butene was 0.01:1. The reaction solution was stirred at 30° C. for 1.5 hours, concentrated by evaporation, and analyzed by nmr spectrum to determine the 1,4:1,2 ratio. The experimental details and results are shown below in Table II below.

ples 21, 22, and 23, a mixture of water and a less polar liquid such as THF can also obtain high 1,4:1,2 ratios. A comparison of Examples 2 and 5 (THF alone as reaction medium) with Examples 21 and 23 (mixture of water and THF), respectively, illustrate that a reaction medium comprising a mixture of water and THF produces higher 1,4:1,2 ratios than THF used alone.

EXAMPLE 5

Methylamine addition to 3,4-epoxy-1-butene using methanol as the reaction medium Methylamine was reacted with 3,4-epoxy-1-butene in methanol as a reaction medium. The catalyst was [($\eta^3$-C$_3$H$_5$)Pd(Ph$_2$P(m-SO$_3$C$_6$H$_4$Na))$_2$](BF$_4$). 0.012 g of catalyst was added to 2 ml of a methylamine in methanol stock solution prepared according to Example 1 (11.5 M). 0.08 ml 3,4-epoxy-1-butene was then added to the solution and the reaction mixture was heated at 30° C. for 1.5 hours. The reaction product was analyzed by NMR. The selectivity (1,4:1,2) was determined to be 5:1.

EXAMPLE 6

Methylamine addition to 3,4-epoxy-1-butene using methylamine in acetonitrile as the reaction medium.

Methylamine was reacted with 3,4-epoxy-1-butene according to the procedure of Example 5 except that methylamine in acetonitrile (11.4M) was used as the reaction medium. The selectivity (1,4:1,2) was determined to be 4:1.

EXAMPLE 7

Methylamine addition to 3,4-epoxy-1-butene using toluene as the reaction medium.

Methylamine was reacted with 3,4-epoxy-1-butene in toluene as a reaction medium. The catalyst included 0.01 g of [($\eta^3$-C$_3$H$_5$)Pd(CH$_3$CN)$_2$](BF$_4$) and 0.0166 g PPh$_3$ were mixed in 0.2 mL CH$_2$C$_{12}$ Methylamine in toluene (2.5 ml, 4.8M) was added. The mixture was frozen and 0.04 ml 3,4-epoxy-1-butene was added. The reaction mixture was kept at 30° C. for 16 hours. The

TABLE II

| Sample | Catalyst | 1,4:1,2 |
|---|---|---|
| 15 | [($\eta^3$-C$_3$H$_5$)Pd((C$_6$H$_5$)$_2$P(m-SO$_3$C$_6$H$_4$)Na))$_2$](BF$_4$) | 26 |
| 16 | [($\eta^3$-C$_3$H$_5$)Pd((C$_6$H$_5$)$_2$P(m-SO$_3$C$_6$H$_4$)Na))$_2$](BF$_4$) | 15 |
| 17 | [($\eta^3$-C$_3$H$_5$)PdCl]$_2$ + 2 eq. (C$_6$H$_5$)$_2$P(m-SO$_3$C$_6$H$_4$)Na | 15 |
| 18 | Na$_2$PdCl$_4$ + 2 eq. (C$_6$H$_5$)$_2$P(m-SO$_3$C$_6$H$_4$)Na | 14 |
| 19 | [(C$_8$H$_{12}$)Pd(CH$_3$CN)$_2$](BF$_4$)** + 2 eq. (C$_6$H$_5$)$_2$P(m-SO$_3$C$_6$H$_4$)Na | 9 |
| 20 | [($\eta^3$-C$_3$H$_5$)Pd(CH$_3$CH)$_2$](BF$_4$) + 2 eq. P(m-SO$_3$C$_6$H$_4$)$_3$K$_3$ | 15 |
| 21 | [($\eta^3$-C$_3$H$_5$)Pd(CH$_3$CN)$_2$](BF$_4$) + 2 eq. P(C$_6$H$_5$)$_3$* | 7 |
| 22 | [($\eta^3$-C$_3$H$_5$)Pd(CH$_3$CN)$_2$](BF$_4$) + 2 eq. (C$_6$H$_5$)$_2$P(CH$_2$)$_2$P(C$_6$H$_5$)$_2$* | 10 |
| 23 | [($\eta^3$-C$_3$H$_5$)Pd(CH$_3$CN)$_2$](BF$_4$) + 2 eq. (C$_4$H$_3$O)$_3$P* | 9.5 |
| 24 | [($\eta^3$-C$_3$H$_5$)Pd(CH$_3$CN)$_2$](BF$_4$) + excess P(O-iso-C$_3$H$_7$)$_3$ | 5.3 |
| 25 | Pd(P(C$_6$H$_5$)$_3$)$_2$Cl$_2$*** | 2.9 |
| 26 | [Pd(CH$_3$CN)$_4$](BF$_4$) + 2 eq. (C$_6$H$_5$)$_2$P(m-SO$_3$C$_6$H$_4$)Na | 2.7 |
| 27 | [Pd(CH$_3$CN)$_4$](BF$_4$) + 4 eq. (C$_6$H$_5$)$_2$P(m-SO$_3$C$_6$H$_4$)Na | 20 |

*0.5 ml THF added to dissolve phosphine ligand.
**This compound was made by adding [Ag(CH$_3$CN)$_4$](BF$_4$) to (C$_8$H$_{12}$)PdCl$_2$ (in 2 to 1 ratio) in dichloromethane. The AgCl precipitate was filtered and the filtrate was concentrated to dryness. C$_8$H$_{12}$ is 1,5-cyclooctadiene.
***Not soluble in water This series of samples shows increased 1,4:1,2 ratios as compared to the preceding examples. This series of samples indicates that high 1,4:1,2 ratios can be obtained by using a highly polar reaction medium (water) and an appropriate catalyst. Furthermore, as shown by Examreaction product was analyzed by gas chromatography. The 1,4 to 1,2 ratio was 3.

EXAMPLE 8

Primary amine or ammonia addition to 3,4-epoxy-1-butene using water as the reaction medium.

Various primary amines and ammonia were reacted with 3,4-epoxy-1-butene according to the procedure described in Example 4, substituting ethylamine (EtNH$_2$), cyclohexylamine (C$_6$H$_{11}$NH$_2$), ammonia (NH$_3$), and ethanolamine (H$_2$NC$_2$H$_5$OH) for methylamine. The ratio of primary amine or ammonia to 3,4-epoxy-1-butene was 20:1, except in the case of C$_6$H$_{11}$NH$_2$, in which the ratio of primary amine to 3,4-epoxy-1-butene was 14:1. The results are shown in Table III below.

TABLE III

| AMINE | [1,4:1,2] |
| --- | --- |
| CH$_3$CH$_2$NH$_2$ | 25 |
| C$_6$H$_{11}$NH$_2$ | 14 |
| NH$_3$ | 6 |
| H$_2$NC$_2$H$_5$OH | 5 |

Table III indicates that the use of water as the reaction medium results in high yields of 1,4-adduct with a variety of primary amines and ammonia.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A process for forming 4-amino-2-buten-1-ol, comprising the steps of:
   providing a quantity of 3,4-epoxy-1-butene;
   providing a quantity of primary amine or ammonia; and
   reacting said quantity of 3,4-epoxy-1-butene with said quantity of primary amine or ammonia in a reaction medium and in the presence of a catalyst, wherein said catalyst is a complex of palladium and phosphine ligands and said reaction medium is a liquid having an $E_T(30)$ no less than about 32.

2. A process according to claim 1, wherein said liquid is selected from the group consisting of toluene, benzene, diethylether, 1,4-dioxane, tetrahydrofuran, and chloroform.

3. A process according to claim 1, wherein said primary amine is methylamine.

4. A process according to claim 1, wherein said liquid has an $E_T(30)$ no less than about 40.

5. A process according to claim 4, wherein said quantity of 3,4-epoxy-1-butene is reacted with a quantity of primary amine selected from the group consisting of methylamine, ethylamine, propylamine, butylamine, hexylamine, octylamine, decylamine, allylamine, 2-hexenylamine, 4-decenylamine, ethanolamine, octanolamine, aniline, and cyclohexylamine.

6. A process according to claim 4, wherein said primary amine is methylamine.

7. A process according to claim 4, wherein said liquid is selected from the group consisting of acetone, dimethylsulfoxide, acetonitrile, nitromethane, 2-propanol, 2-methoxyethanol, N-methylformamide, methanol, 1,2-ethanediol, glycerol, ethanol, 2,2,2-trifluoroethanol, water, and an 80:20 solution of ethanol and water.

8. A process according to claim 1, wherein said liquid has an $E_T(30)$ no less than about, 45.

9. A process according to claim 8, wherein said quantity of 3,4-epoxy-1-butene is reacted with a quantity of primary amine selected from the group consisting of methylamine, ethylamine, propylamine, butylamine, hexylamine, octylamine, decylamine, allylamine, 2-hexenylamine, 4-decenylamine, ethanolamine, octanolamine, aniline, and cyclohexylamine.

10. A process according to claim 8, wherein said primary amine is methylamine.

11. A process according to claim 8, wherein said liquid is selected from the group consisting of 2-methoxyethanol, N-methylformamide, methanol, dimethyl sulfoxide, acetonitrile, nitromethane, 2-propanol, ethanol, glycerol, 1,2-ethanediol, 2,2,2-trifluoroethanol, water, and an 80:20 solution of ethanol and water.

12. A process according to claim 1, wherein said liquid is water.

13. A process according to claim 12, wherein said quantity of 3,4-epoxy-1-butene is reacted with a quantity of primary amine selected from the group consisting of methylamine, ethylamine, propylamine, butylamine, hexylamine, octylamine, decylamine, allylamine, 2-hexenylamine, 4-decenylamine, ethanolamine, octanolamine, aniline, and cyclohexylamine.

14. A process according to claim 12, wherein said primary amine is methylamine.

15. A process according to claim 3, wherein said liquid is methylamine.

16. A process according to claim 1, wherein said catalyst is selected from the group consisting of:
   Pd(PR$_1$R$_2$R$_3$)$_2$X$_2$;
   Pd(R$_4$R$_5$P(V)$_b$ZR$_6$R$_7$)X$_2$;
   [($\eta^3$-CH(R$_8$)C(R$_9$)CH(R$_{10}$))Pd(PR$_1$R$_2$R$_3$)$_2$]X;
   [($\eta^3$-CH(R$_8$)C(R$_9$)CH(R$_{10}$))Pd(R$_4$R$_5$P(V)$_b$ZR$_6$R$_7$)]X;
   Pd(R$_4$R$_5$P(V)$_b$ZR$_6$R$_7$)$_2$;
   Pd(PR$_1$R$_2$R$_3$)$_4$;
   [Pd(D)(PR$_1$R$_2$R$_3$)$_2$]X$_2$; and
   [Pd(D)R$_4$R$_5$(V)$_b$ZR$_6$R$_7$)]X$_2$;
wherein
   R$_1$, R$_2$, R$_3$, R$_4$, R$_5$, R$_6$, and R$_7$ can be the same or different and each are an alkyl, cycloalkyl, alkoxide, aryl, heterocyclic, functionalized alkyl, functionalized aryl, or ether group;
   R$_8$, R$_9$, and R$_{10}$ are the same or different and each are hydrogen, alkyl, cycloalkyl, aryl, heterocyclic, halogen, ether, sulfide, carbonyl or are linked together to form a ring;
   V is CH$_2$ or CH as part of unsaturated component;
   Z is phosphorus or nitrogen;
   D is a cyclic diene;
   X is an anion;
   Ph is a phenyl group;
   P is phosphorus;
   Pd is palladium; and
   b is a number in the range from 1 to 4.

17. A process according to claim 1, wherein said liquid is water or a mixture of liquids including water and said catalyst is selected from the group consisting of:
   Pd(Ph$_2$P(m-C$_6$H$_4$SO$_3$Q))$_2$X$_2$, Pd(P(m-C$_6$H$_4$SO$_3$Q))$_3$)$_2$X$_2$,
   Pd(Ph$_2$P(o-CO$_2$C$_6$H$_4$Q))$_2$X$_2$,
   Pd(P(CH$_2$CH$_2$(CH$_2$CH$_2$O)$_a$CH$_3$)$_3$)$_2$X$_2$,
   Pd(PhP(CH$_2$CH$_2$CH$_2$OCH$_3$)$_2$)$_2$X$_2$,
   Pd(Ph$_2$PCH$_2$CH$_2$N(CH$_3$)$_3$X)$_2$X$_2$,
   Pd(Ph$_2$PCH$_2$CH$_2$CO$_2$Q)X$_2$,
   Pd[(C$_6$H$_5$)$_2$P(CH$_2$)$_2$N(CH$_3$)$_2$]X$_2$, Pd[(m-SO$_3$C$_6$H$_4$Q)$_c$(C$_6$H$_5$)$_{2-c}$P(CH$_2$)$_d$P(C$_6$H$_5$)$_f$(m-SO$_3$C$_6$H$_4$Q)$_{2-f}$]X$_2$,
Pd[(m-SO$_3$C$_6$H$_4$Q)$_c$(C$_6$H$_5$)$_{2-c}$PCH(CH$_3$)CH(CH$_3$)P(C$_6$H$_5$)$_f$(m-SO$_3$C$_6$H$_4$Q)$_{2-f}$]X$_2$,
Pd[(p-(CH$_3$)$_3$NC$_6$H$_4$X)$_2$PC$_2$H$_4$P(p-(CH$_3$)$_3$NC$_6$H$_4$X)$_2$]X$_2$,
Pd[(P-(CH$_3$)$_3$NC$_6$H$_4$X)$_2$PCH(CH$_3$)CH(CH$_3$)P(p-(CH$_3$)$_3$NC$_6$H$_4$X)$_2$]X$_2$, and $$Pd(CH_3[OCH_2CH_2]_eOC(=O)-N(C_2H_4PPh_2)_2)X_2,$$

[($\eta^3$-C$_3$H$_5$)Pd(P(m-C$_6$H$_4$SO$_3$Q))$_3$)$_2$]X, [($\eta^3$-C$_3$H$_5$)Pd(Ph$_2$P(m-C$_6$H$_4$SO$_3$Q))$_2$]X, [($\eta^3$-C$_3$H$_5$)Pd(Ph$_2$P(m-C$_6$H$_4$CO$_2$Q))$_2$]X, [($\eta^3$-C$_3$H$_5$)Pd(P(CH$_2$(CH$_2$CH$_2$O)$_a$CH$_3$)$_3$)$_2$]X, [($\eta^3$-C$_3$H$_5$)Pd(PhP(CH$_2$CH$_2$CH$_2$OCH$_3$)$_2$)$_2$]X, [($\eta^3$-C$_3$H$_5$)Pd(Ph$_2$PCH$_2$CH$_2$N(CH$_3$)$_3$X)$_2$]X, [($\eta^3$-C$_3$H$_5$)Pd(P(O-iso-C$_3$H$_7$)$_3$)$_2$]X, [($\eta^3$-C$_3$H$_5$)Pd[(m-SO$_3$C$_6$H$_4$Q)$_c$(C$_6$H$_5$)$_{2-c}$P(CH$_2$)$_d$P(C$_6$H$_5$)$_f$(m-SO$_3$C$_6$H$_4$Q))$_{2-f}$]X, [($\eta^3$-C$_3$H$_5$)Pd(p-(CH$_3$)$_3$NC$_6$H$_4$X)$_2$PC$_2$H$_4$P(p-(CH$_3$)$_3$NC$_6$H$_4$X)$_2$]X, [($\eta^3$-C$_3$H$_5$)Pd(p-(CH$_3$)$_3$NC$_6$H$_4$X)$_2$PCH(CH$_3$)CH(CH$_3$)P(p-(CH$_3$)$_3$NC$_6$H$_4$, X)$_2$]X, Pd[(C$_6$H$_5$)$_2$P(CH$_2$)$_2$N(CH$_3$)$_2$]$_2$, Pd(P(m-C$_6$H$_4$SO$_3$Q)$_3$)$_4$, Pd[Ph$_2$P(m-SO$_3$C$_6$H$_4$Q)]$_3$, Pd[Ph$_2$P(m-SO$_3$C$_6$H$_4$Q)]$_4$, Pd[P(CH$_2$(CH$_2$CH$_2$O)$_a$CH$_3$)$_3$]$_4$, Pd[P(CH(CH$_3$)(CH$_2$CH$_2$O)$_3$CH$_3$)$_3$]$_4$, Pd[PhP(CH$_2$CH$_2$CH$_2$OCH$_3$)$_2$]$_4$, Pd[Ph$_2$PCH$_2$CH$_2$N(CH$_3$)$_3$X]$_4$, Pd[(p-(CH$_3$)$_3$NC$_6$H$_4$X)$_2$PCH(CH$_3$)CH(CH$_3$)P(p-(CH$_3$)$_3$NC$_6$H$_4$X)$_2$]$_2$, Pd[(p-(CH$_3$)$_3$NC$_6$H$_4$X)$_2$PC$_2$H$_4$P(p-(CH$_3$)$_3$NC$_6$H$_4$X)$_2$]$_2$, and Pd[(m-SO$_3$C$_6$H$_4$Q)$_c$(C$_6$H$_5$)$_{2-c}$P(CH$_2$)$_d$P(C$_6$H$_5$)$_f$(m-SO$_3$C$_6$H$_4$Q)$_{2-f}$]$_2$, [(C$_8$H$_{12}$)Pd(P(m-C$_6$H$_4$SO$_3$Q)$_3$)$_2$]X$_2$, [(C$_7$H$_8$)Pd(P(CH$_2$(CH$_2$CH$_2$O)$_a$CH$_3$)$_3$)$_2$]X$_2$, [(C$_7$H$_8$)Pd(PhP(CH$_2$CH$_2$CH$_2$OCH$_3$)$_2$)$_2$]X$_2$, [(C$_7$H$_8$)Pd(Ph$_2$PCH$_2$CH$_2$N(CH$_3$)$_3$X)$_2$]X$_2$, [(C$_7$H$_8$)Pd((C$_6$H$_5$)$_2$P(m-SO$_3$C$_6$H$_4$Q))$_2$]X$_2$, [(C$_7$H$_8$)Pd(P(m-SO$_3$C$_6$H$_4$Q)$_3$)$_2$]X$_2$, [(C$_8$H$_{12}$)Pd(P(CH$_2$(CH$_2$CH$_{20}$)$_a$CH$_3$)$_3$)$_2$]X$_2$, [(C$_8$H$_{12}$)Pd(PhP(CH$_2$CH$_2$CH$_{20}$CH$_3$)$_2$)$_2$]X$_2$, [(C$_7$H$_8$)Pd((p-(CH$_3$)$_3$NC$_6$H$_4$X)$_2$PCH(CH$_3$)CH(CH$_3$)P(p-(CH$_3$)$_3$NC$_6$H$_4$X)$_2$]X$_2$, [(C$_7$H$_8$)Pd(m-SO$_3$C$_6$H$_4$Q)$_c$(C$_6$H$_5$)$_{2-c}$P(CH$_2$)$_d$P(C$_6$H$_5$)$_f$(m-SO$_3$C$_6$H$_4$Q)$_{2-f}$]X$_2$, [(C$_7$H$_8$)Pd(p-(CH$_3$)$_3$NC$_6$H$_4$X)$_2$PC$_2$H$_4$P(p-(CH$_3$)$_3$NC$_6$H$_4$X)$_2$]X$_2$, $$[(C_7H_8)Pd(CH_3[OCH_2CH_2]_eOC(=O)-N(C_2H_4PPh_2)_2)]X_2,$$

[(C$_7$H$_8$)Pd(m-SO$_3$C$_6$H$_4$Q)$_c$(C$_6$H$_5$)$_{2-c}$PCH(CH$_3$)CH(CH$_3$)P(C$_6$H$_5$)$_f$(m-SO$_3$C$_6$H$_4$Q)$_{2-f}$]X$_2$, [(C$_8$H$_{12}$)Pd((p-(CH$_3$)$_3$NC$_6$H$_4$X)$_2$PCH(CH$_3$)CH(CH$_3$)P(p-(CH$_3$)$_3$NC$_6$H$_4$X)$_2$]X$_2$, [(C$_8$H$_{12}$)Pd(p-(CH$_3$)$_3$NC$_6$H$_4$X)$_2$PC$_2$H$_4$P(p-(CH$_3$)$_3$NC$_6$H$_4$X)$_2$]X$_2$, $$[(C_8H_{12})Pd(CH_3[OCH_2CH_2]_eOC(=O)-N(C_2H_4PPh_2)_2)]X_2,$$

[(C$_8$H$_{12}$)Pd(m-SO$_3$C$_6$H$_4$Q)$_c$(C$_6$H$_5$)$_{2-c}$P(CH$_2$)$_d$P(C$_6$H$_5$)$_f$(m-SO$_3$C$_6$H$_4$Q)$_{2-c}$]X$_2$, [(C$_8$H$_{12}$)Pd(p-(CH$_3$)$_3$NC$_6$H$_4$X)$_2$PC$_2$H$_4$P(p-(CH$_3$)$_3$NC$_6$H$_4$X)$_2$]X$_2$, [(C$_8$H$_{12}$)Pd(m-SO$_3$C$_6$H$_4$Q)$_c$(C$_6$H$_5$)$_{2-c}$PCH(CH$_3$)CH(CH$_3$)P(C$_6$H$_5$)$_f$(m-SO$_3$C$_6$H$_4$Q)$_{2-f}$]X$_2$, wherein Ph is a phenyl group, P is phosphorus, Pd is palladium, a is a number in the range from 1 to 3, b is a number in the range from 1 to 4, c and f are 1 or 2, d is a number in the range from 2 to 4, e is 12 or 16, Q is a cation, and X is an anion.

18. A process for forming 4-amino-2-buten-1-ol, comprising the steps of:
providing a quantity of 3,4-epoxy-1-butene;
providing a quantity of a primary amine selected from the group consisting of methylamine and cyclohexylamine; and
reacting said quantity of 3,4-epoxy-1-butene with said quantity of methylamine in a reaction medium and in the presence of a catalyst, wherein said catalyst is selected from the group consisting of:
Pd(PR$_1$R$_2$R$_3$)$_2$X$_2$;
Pd(R$_4$R$_5$P(V)$_b$ZR$_6$R$_7$)X$_2$;
[($\eta^3$-CH(R$_8$)C(R$_9$)CH(R$_{10}$))Pd(PR$_1$R$_2$R$_3$)$_2$]X;
[($\eta^3$-CH(R$_8$)C(R$_9$)CH(R$_{10}$))Pd(R$_4$R$_5$P(V)$_b$ZR$_6$R$_7$)]X;
Pd(R$_4$R$_5$P(V)$_b$ZR$_6$R$_7$)$_2$;
Pd(PR$_1$R$_2$R$_3$)$_4$;
[Pd(D)(PR$_1$R$_2$R$_3$)$_2$]X$_2$; and
[Pd(D)R$_4$R$_5$(V)$_b$ZR$_6$R$_7$)]X$_2$;
wherein
R$_1$, R$_2$, R$_3$, R$_4$, R$_5$, R$_6$, and R$_7$ can be the same or different and each are an alkyl, cycloalkyl, alkoxide, aryl, heterocyclic, functionalized alkyl, functionalized aryl, or ether group;
R$_8$, R$_9$, and R$_{10}$ are the same or different and each are hydrogen, alkyl, cycloalkyl, aryl, heterocyclic, halogen, ether, sulfide, carbonyl or are linked together to form a ring;
V is CH$_2$ or CH as part of unsaturated component;
Z is phosphorus or nitrogen;
D is a cyclic diene;
X is an anion;
Ph is a phenyl group;
P is phosphorus;
Pd is palladium; and
b is a number in the range from 1 to 4; and
wherein said reaction medium is selected from the group consisting of 2-methoxyethanol, N-methylformamide, methanol, dimethyl sulfoxide, acetonitrile, nitromethane, 2-propanol, ethanol, glycerol, 1,2-ethanediol, 2,2,2-trifluoroethanol, water, and an 80:20 solution of ethanol and water.

19. A process according to claim 4, wherein said 3,4-epoxy-1-butene is reacted with a quantity of ammonia.

20. A process according to claim 8, wherein said 3,4-epoxy-1-butene is reacted with a quantity of ammonia.

21. A process according to claim 12, wherein said 3,4-epoxy-1-butene is reacted with a quantity of ammonia.

* * * * *

UNITED STATES PATENT AND TRADEMARK OFFICE
CERTIFICATE OF CORRECTION

PATENT NO. : 5,288,910
DATED : February 22, 1994
INVENTOR(S) : Hung

It is certified that error appears in the above-identified patent and that said Letters Patent is hereby corrected as shown below:

Column 11, line 33 (Claim 1, line 1), after "4-amino-", --- substituted- --- should be inserted.

Column 11, line 68 (Claim 8, line 2), after "about", the comma (,) should be deleted.

Column 13, line 46 (Claim 17),
"$[(C_8H_{12})Pd(P(CH_2(CH_2CH_2O)_aCH_3)_3)_2]X_2,$" should be
--- $[(C_8H_{12})Pd(P(CH_2(CH_2CH_2O)_aCH_3)_3)_2]X_2,$ ---.

Column 13, line 47 (Claim 17),
"$[(C_8H_{12})Pd(PhP(CH_2CH_2CH_2OCH_3)_2)_2]X_2,$" should be
--- $[(C_8H_{12})Pd(PhP(CH_2CH_2CH_2OCH_3)_2)_2]X_2,$ ---.

Column 13, line 64 (Claim 17), "$(CH_3)_3NC_6H_4X\quad _2]X_2,$
$[(C_8H_{12})Pd(\underline{p}-$" should be --- $(CH_3)_3NC_6H_4X)_2]X_2,$
$[(C_8H_{12})Pd(\underline{p}-$ ---.

Column 14, line 15 (Claim 18, line 1), after "4-amino-", --- substituted- --- should be inserted.

Signed and Sealed this

Ninth Day of August, 1994

Attest:

BRUCE LEHMAN

*Attesting Officer*   Commissioner of Patents and Trademarks